United States Patent
Hong et al.

(10) Patent No.: US 10,306,410 B2
(45) Date of Patent: May 28, 2019

(54) MOBILE DEVICES, METHODS FOR CONTROLLING A MOBILE DEVICE, AND COMPUTER READABLE MEDIA

(71) Applicant: RAZER (ASIA-PACIFIC) PTE. LTD., Singapore (SG)

(72) Inventors: Sze Wei Joel Hong, Singapore (SG); Liangqin Mark Tay, Singapore (SG)

(73) Assignee: RAZER (ASIA-PACIFIC) PTE. LTD., Singapore (SG)

( * ) Notice: Subject to any disclaimer, the term of this patent is extended or adjusted under 35 U.S.C. 154(b) by 0 days.

(21) Appl. No.: 15/739,104

(22) PCT Filed: Jun. 25, 2015

(86) PCT No.: PCT/SG2015/050182
§ 371 (c)(1),
(2) Date: Dec. 21, 2017

(87) PCT Pub. No.: WO2016/209162
PCT Pub. Date: Dec. 29, 2016

(65) Prior Publication Data
US 2018/0176736 A1  Jun. 21, 2018

(51) Int. Cl.
*H04W 4/024* (2018.01)
*G06Q 50/22* (2018.01)
*H04W 4/029* (2018.01)
*A63B 24/00* (2006.01)

(52) U.S. Cl.
CPC ......... *H04W 4/024* (2018.02); *A63B 24/0021* (2013.01); *A63B 24/0062* (2013.01); *A63B 24/0084* (2013.01); *G06Q 50/22* (2013.01); *H04W 4/029* (2018.02)

(58) Field of Classification Search
CPC ............ A63B 24/0021; A63B 24/0062; A63B 24/0084; H04W 4/024; H04W 4/029; G06Q 50/22
See application file for complete search history.

(56) References Cited

U.S. PATENT DOCUMENTS

| | | | |
|---|---|---|---|
| 6,013,007 | A | 1/2000 | Root et al. |
| 6,837,827 | B1 | 1/2005 | Lee et al. |
| 7,292,867 | B2 | 11/2007 | Werner et al. |

(Continued)

FOREIGN PATENT DOCUMENTS

| | | |
|---|---|---|
| KR | 10-2012-0114212 A | 10/2012 |
| WO | 2001/061671 A1 | 8/2001 |
| WO | WO 2010/064178 A1 | 6/2010 |

OTHER PUBLICATIONS

Extended European Search Report dated Dec. 5, 2018, 11 pages, for the corresponding European Patent Application No. 15896488.2.

*Primary Examiner* — Nathan S Taylor
(74) *Attorney, Agent, or Firm* — Polsinelli PC

(57) ABSTRACT

According to various embodiments, a mobile device may be provided. The mobile device may include: a location determination circuit configured to determine a location of the mobile device; a goal determination circuit configured to determine a goal of a user of the mobile device; a target determination circuit configured to determine a target based on the determined location and based on the determined goal; and a notification circuit configured to notify the user about the target.

13 Claims, 1 Drawing Sheet

(56) References Cited

U.S. PATENT DOCUMENTS

| | | | |
|---|---|---|---|
| 7,328,119 B1 | 2/2008 | Pryor et al. | |
| 7,398,151 B1 | 7/2008 | Burrell et al. | |
| 7,603,255 B2 | 10/2009 | Case, Jr. et al. | |
| 8,109,858 B2 | 2/2012 | Redmann | |
| 8,562,490 B2 | 10/2013 | Dibenedetto et al. | |
| 8,690,578 B1 | 4/2014 | Nusbaum et al. | |
| 2008/0009275 A1* | 1/2008 | Werner | A63B 24/0062 455/414.2 |
| 2008/0096726 A1* | 4/2008 | Riley | A63B 24/0006 482/8 |
| 2009/0118100 A1* | 5/2009 | Oliver | A63B 24/0062 482/8 |
| 2010/0088023 A1* | 4/2010 | Werner | A63B 24/0021 701/467 |
| 2010/0127926 A1 | 5/2010 | Wang | |
| 2011/0054779 A1* | 3/2011 | Kim | G01C 21/3484 701/533 |
| 2011/0098928 A1* | 4/2011 | Hoffman | A63B 24/0062 702/5 |
| 2011/0124978 A1 | 5/2011 | Williams | |
| 2011/0197157 A1* | 8/2011 | Hoffman | A63B 24/0062 715/772 |
| 2011/0270522 A1* | 11/2011 | Fink | G09G 5/377 701/532 |
| 2012/0010809 A1* | 1/2012 | Stut | G06F 19/3481 701/465 |
| 2012/0015778 A1* | 1/2012 | Lee | A63B 71/0622 482/8 |
| 2012/0089465 A1 | 4/2012 | Froloff | |
| 2012/0116550 A1* | 5/2012 | Hoffman | A63B 24/0084 700/91 |
| 2013/0030889 A1 | 1/2013 | Davich et al. | |
| 2013/0238287 A1* | 9/2013 | Hoffman | A63B 24/0062 702/189 |
| 2013/0330694 A1 | 12/2013 | Watterson | |
| 2014/0127649 A1* | 5/2014 | Utter, II | G16H 20/60 434/127 |
| 2014/0212855 A1* | 7/2014 | Robinson | G09B 19/00 434/247 |
| 2014/0228987 A1* | 8/2014 | Case, Jr. | A63B 24/00 700/91 |
| 2014/0276244 A1 | 9/2014 | Kamyar | |
| 2015/0042468 A1* | 2/2015 | White | G16H 20/30 340/539.11 |
| 2015/0066683 A1* | 3/2015 | Azose | G06Q 30/0631 705/26.7 |
| 2015/0081062 A1* | 3/2015 | Fyfe | G06F 19/3481 700/91 |
| 2016/0351072 A1* | 12/2016 | Nusbaum | G09B 19/00 |

\* cited by examiner

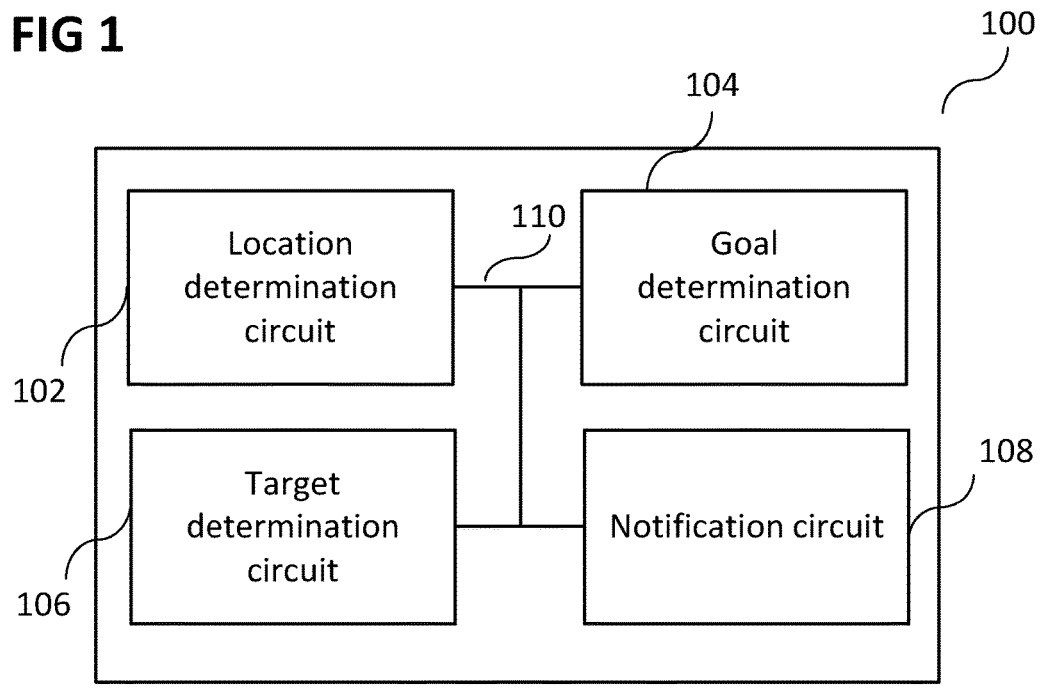
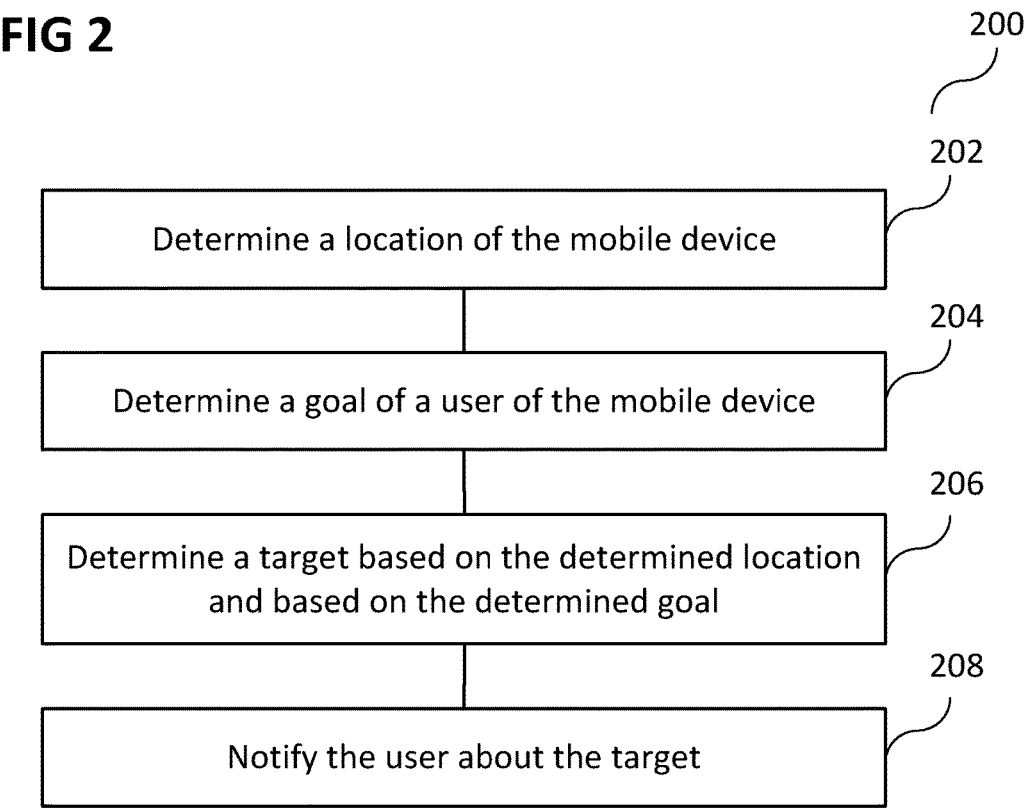

MOBILE DEVICES, METHODS FOR CONTROLLING A MOBILE DEVICE, AND COMPUTER READABLE MEDIA

TECHNICAL FIELD

Various embodiments generally relate to mobile devices, methods for controlling a mobile device, and computer readable media.

BACKGROUND

Fitness apps (in other words: applications) may allow users to predefine health/fitness related goals in order to improve overall health or fitness. This goal may be in the form of number of steps per day. The apps may notify the user on the number of steps achieved per day and how it measures against the predefined fitness/health goals. For example, the app may show the user that he has exceeded the number of steps taken or he has fallen short of the number of steps taken. In the case of underachievement, the app may show the user how far he is away from his goal. Commonly used fitness apps however do not provide users with the motivation to accomplish/overachieve predefined activity/health related goals/objectives. Thus, there may be a need for devices and methods providing motivation to users.

SUMMARY OF THE INVENTION

According to various embodiments, a mobile device may be provided. The mobile device may include: a location determination circuit configured to determine a location of the mobile device; a goal determination circuit configured to determine a goal of a user of the mobile device; a target determination circuit configured to determine a target based on the determined location and based on the determined goal; and a notification circuit configured to notify the user about the target.

According to various embodiments, a method for controlling a mobile device may be provided. The method may include: determining a location of the mobile device; determining a goal of a user of the mobile device; determining a target based on the determined location and based on the determined goal; and notifying the user about the target.

According to various embodiments, a computer readable medium may be provided. The computer readable medium may include program instructions which when executed by a processor of a mobile device cause the processor to perform: determining a location of the mobile device; determining a goal of a user of the mobile device; determining a target based on the determined location and based on the determined goal; and notifying the user about the target.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. The dimensions of the various features or elements may be arbitrarily expanded or reduced for clarity. In the following description, various embodiments of the invention are described with reference to the following drawings, in which:

FIG. 1 shows a mobile device according to various embodiments; and

FIG. 2 shows a flow diagram illustrating a method for controlling a mobile device according to various embodiments.

DETAILED DESCRIPTION

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

In this context, the mobile device as described in this description may include a memory which is for example used in the processing carried out in the mobile device. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

In the specification the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

The reference to any prior art in this specification is not, and should not be taken as an acknowledgement or any form of suggestion that the referenced prior art forms part of the common general knowledge in Australia (or any other country).

In order that the invention may be readily understood and put into practical effect, particular embodiments will now be described by way of examples and not limitations, and with reference to the figures.

Various embodiments are provided for devices, and various embodiments are provided for methods. It will be understood that basic properties of the devices also hold for the methods and vice versa. Therefore, for sake of brevity, duplicate description of such properties may be omitted.

It will be understood that any property described herein for a specific device may also hold for any device described herein. It will be understood that any property described herein for a specific method may also hold for any method described herein. Furthermore, it will be understood that for any device or method described herein, not necessarily all the components or steps described must be enclosed in the device or method, but only some (but not all) components or steps may be enclosed.

The term "coupled" (or "connected") herein may be understood as electrically coupled or as mechanically coupled, for example attached or fixed or attached, or just in contact without any fixation, and it will be understood that both direct coupling or indirect coupling (in other words: coupling without direct contact) may be provided.

Fitness apps (in other words: applications) may be provided on a wearable device such as a fitness band (for example NABU) or on a mobile device which provides the fitness apps. Fitness apps may allow tracking of user activity and/or location for a user to monitor the overall health and activity of the user.

Fitness apps may allow users to predefine health/fitness related goals in order to improve overall health or fitness. This goal may be in the form of number of steps per day. The apps may notify the user on the number of steps achieved per day and how it measures against the predefined fitness/health goals. For example, the app may show the user that he has exceeded the number of steps taken or he has fallen short of the number of steps taken. In the case of underachievement, the app may show the user how far he is away from his goal. Commonly used fitness apps however do not provide users with the motivation to accomplish and/or overachieve predefined activity and/or health related goals (in other words: objectives).

According to various embodiments, devices and methods may be provided which provide motivation to users.

According to various embodiments, devices and methods may be provided which provide the user with a visualized motivation to accomplish and/or overachieve predefined fitness related goals.

FIG. 1 shows a mobile device 100 according to various embodiments. The mobile device 100 may include a location determination circuit 102 configured to determine a location of the mobile device 100. The mobile device 100 may further include a goal determination circuit 104 configured to determine a goal of a user of the mobile device 100. The mobile device 100 may further include a target determination circuit 106 configured to determine a target based on the determined location and based on the determined goal. The mobile device 100 may further include a notification circuit 108 configured to notify the user about the target. The location determination circuit 102, the goal determination circuit 104, the target determination circuit 106, and the notification circuit 108 may be coupled with each other, like indicated by lines 110, for example electrically coupled, for example using a line or a cable, and/or mechanically coupled.

In other words, according to various embodiments, a mobile device may notify a user about a target to proceed to (for example: to walk to; or to run to; or to swim to; or to ride to by bicycle), in order for the user to achieve his personal fitness goal.

According to various embodiments, the goal may include or may be a fitness goal and/or a goal related to amount of exercise and/or a goal related to distance walked and/or a goal related to energy consumption and/or a goal related to steps taken.

According to various embodiments, the target may include or may be a building and/or a park and/or a shop and/or a shopping center and/or an office and/or a street and/or a district of a city and/or a city and/or a country and/or a state.

According to various embodiments, the notification circuit 108 may be configured to notify the user with an indication related to fulfillment of the goal if the user moves to the determined target.

According to various embodiments, the location determination circuit 102 may be configured to determine the location of the mobile device 100 using GPS (Global Positioning System) and/or WiFi triangulation and/or mobile radio communication cell triangulation.

According to various embodiments, the target determination circuit 106 may be configured to determine the target so that the determined goal is fulfilled if the user moves to the target.

According to various embodiments, the target determination circuit 106 may be configured to determine a plurality of targets so that the determined goal is fulfilled if the user moves (for example sequentially moves) to the plurality of targets.

According to various embodiments, the target determination circuit 106 may be configured to determine a plurality of targets and a sequence of the plurality of targets so that the determined goal is fulfilled if the user moves to the plurality of targets in the sequence.

According to various embodiments, the notification circuit 108 may be configured to notify the user visually.

According to various embodiments, the mobile device 100 may include or may be or may be included in a mobile radio communication device and/or a mobile phone and/or a tablet computer and/or a handheld device and/or a wearable device (for example a wristband).

According to various embodiments, the target determination circuit 106 may further be configured to determine the target further based on traffic conditions.

According to various embodiments, the target determination circuit 106 may further be configured to determine the target further based on weather conditions.

According to various embodiments, the target determination circuit 106 may further be configured to determine the target further based on a time left to complete the goal.

FIG. 2 shows a flow diagram 200 illustrating a method for controlling a mobile device according to various embodiments. In 202, a location of the mobile device may be determined. In 204, a goal of a user of the mobile device may be determined. In 206, a target may be determined based on the determined location and based on the determined goal. In 208, the user may be notified about the target.

According to various embodiments, the goal may include or may be a fitness goal and/or a goal related to amount of exercise and/or a goal related to distance walked and/or a goal related to energy consumption and/or a goal related to steps taken.

According to various embodiments, the target may include or may be a building and/or a park and/or a shop and/or a shopping center and/or an office and/or a street and/or a district of a city and/or a city and/or a country and/or a state.

According to various embodiments, notifying the user may include or may be notifying the user with an indication related to fulfillment of the goal if the user moves to the determined target.

According to various embodiments, determining the location may include or may be determining the location of the mobile device using at least one of GPS, WiFi triangulation, and mobile radio communication cell triangulation.

According to various embodiments, determining the target may include or may be determining the target so that the determined goal is fulfilled if the user moves to the target.

According to various embodiments, the method may further include determining a plurality of targets so that the determined goal is fulfilled if the user moves to the plurality of targets.

According to various embodiments, the method may further include determining a plurality of targets and a sequence of the plurality of targets so that the determined goal is fulfilled if the user moves to the plurality of targets in the sequence.

According to various embodiments, notifying the user may include or may be notifying the user visually.

According to various embodiments, the mobile device may include or may be or may be included in a mobile radio communication device and/or a mobile phone and/or a tablet computer and/or a handheld device and/or a wearable device.

According to various embodiments, the method may further include determining the target further based on traffic conditions.

According to various embodiments, the method may further include determining the target further based on weather conditions.

According to various embodiments, the method may further include determining the target further based on a time left to complete the goal.

According to various embodiments, a computer readable medium may be provided including program instructions which when executed by a processor of a mobile device cause the processor to perform: determining a location of the mobile device; determining a goal of a user of the mobile device; determining a target based on the determined location and based on the determined goal; and notifying the user about the target.

According to various embodiments, the goal may include or may be a fitness goal and/or a goal related to amount of exercise and/or a goal related to distance walked and/or a goal related to energy consumption and/or a goal related to steps taken.

According to various embodiments, the target may include or may be a building and/or a park and/or a shop and/or a shopping center and/or an office and/or a street and/or a district of a city and/or a city and/or a country and/or a state.

According to various embodiments, notifying the user may include or may be notifying the user with an indication related to fulfillment of the goal if the user moves to the determined target.

According to various embodiments, determining the location may include or may be determining the location of the mobile device using at least one of GPS, WiFi triangulation, and mobile radio communication cell triangulation.

According to various embodiments, determining the target may include or may be determining the target so that the determined goal is fulfilled if the user moves to the target.

According to various embodiments, the computer readable medium may further include program instructions which when executed by the processor of the mobile device cause the processor to perform determining a plurality of targets so that the determined goal is fulfilled if the user moves to the plurality of targets.

According to various embodiments, the computer readable medium may further include program instructions which when executed by the processor of the mobile device cause the processor to perform: determining a plurality of targets and a sequence of the plurality of targets so that the determined goal is fulfilled if the user moves to the plurality of targets in the sequence.

According to various embodiments, notifying the user may include or may be notifying the user visually.

According to various embodiments, the mobile device may include or may be or may be included in a mobile radio communication device and/or a mobile phone and/or a tablet computer and/or a handheld device and/or a wearable device.

According to various embodiments, the computer readable medium may further include program instructions which when executed by the processor of the mobile device cause the processor to perform determining the target further based on traffic conditions.

According to various embodiments, the computer readable medium may further include program instructions which when executed by the processor of the mobile device cause the processor to perform determining the target further based on weather conditions.

According to various embodiments, the computer readable medium may further include program instructions which when executed by the processor of the mobile device cause the processor to perform determining the target further based on a time left to complete the goal.

According to various embodiments, devices and methods related to fitness tracker goals may be provided.

According to various embodiments, devices and methods related to fitness goals with wearable devices may be provided.

According to various embodiments, visualized motivation may take the form of notification to the user how far he is short of his goals and how he can achieve his goals. For example, a notification could be "You only need to walk to ABC Subway station in order to achieve this goal". According to various embodiments, a GPS (Global Positioning System) tracker (which for example may be provided in the mobile device or wearable device) may identify the user's current location and may calculate the nearest public place of interest/destination in order to achieve his goal.

According to various embodiments, the user may be provided with a visualized motivation in the form of regional/targeted marketing, for example "You only need to walk to ABC Bistro Café/ABC Shopping Mall in order to achieve your goal". The GPS tracker may identify the user's current location and may calculate the nearest market participant or merchants in order to achieve this goal. The merchant may also provide information in the form of deals or discounts to the user as a form of incentive to achieve this goal.

According to various embodiments, a method of accomplishing a fitness goal on a fitness-related application may include the following (for example the following steps):

1. Identifying location of user;
2. Monitoring user activity of user such that when user activity reaches a predetermined level of user activity;
3. Notify the user with a visual notification on shortfall or accomplishment in achieving fitness goal.

According to various embodiments, where a shortfall or achievement is identified, the user may be notified to walk to the nearest place of interest to achieve or overachieve his fitness goal.

According to various embodiments, where a shortfall or achievement is identified, the user may be notified to walk to the nearest participating merchant to achieve or overachieve his fitness goal.

According to various embodiments, weather and traffic conditions may be checked (for example in suggested destinations or activities to achieve goals), and a target (in other words: target location) may be determined based on these conditions. According to various embodiments, the target may be determined based on an element of time left to complete the goal and a percentage of the goal left to achieve the goal.

According to various embodiments, a goal may include a goal related to steps taken, and/or calories used, and/or distance walked, and/or distance cycled, and/or floors climbed.

According to various embodiments, to gain steps and/or calorie and/or distance walked goals, a target may be a café; for example a user may be instructed (in other words: told; in other words: notified) to go to a nearby café for a take-out to complete the last 100 steps to the goal. This may be also used for promotions of participating café s or for advertising café s.

According to various embodiments, to gain steps and/or calorie and/or distance walked goals, a target may be a nearby attraction; for example, a user may be instructed (in other words: told; in other words: notified) to go to a nearby attraction (e.g. a museum that has a free day). This may also be used for tourism and promoting local events. Walking around in a museum may help achieve a large percentage of steps to complete the goal.

According to various embodiments, to gain steps and/or calorie and/or distance walked goals, a target may be a grocery or a mall. According to various embodiments, a user may be notified about a shopping list in an IOT (Internet of things) environment. For example, a user may be instructed (in other words: told; in other words: notified) to go out to mall to buy. This may cover a situation of large land areas that requires driving to, where achieving of steps may pertain to walking around during shopping. According to various embodiments, an application (app) may plan a route in a mall to get items in suggestion to complete the goal.

According to various embodiments, to gain cycling goals, a route may be suggested to a user, and traffic conditions to (or in) a suggested route may be compared.

According to various embodiments, to hit floor goals, it may be suggested to a user to stop (for example stop with the elevator) at a certain floor to climb to the office. According to various embodiments, a system may be provided which understands (in other words: knows; in other words: has stored information about) a destination floor of the user (for example a floor (for example floor number) of an office (for example an office of the user or an office to which the user is heading)).

According to various embodiments, device and methods may be provided for accomplishing fitness goals on a mobile (for example wearable) device.

According to various embodiments, a wearable device may be provided that maintains awareness of a user's personal fitness goals by motivating the user through known fitness data and combining marketing incentives to help motivate the user. The device may not only provide tracking of user activity and/or location for user to monitor the overall health and activity, but may also provide motivation for the user by allowing the user to set fitness goals and then attempt to achieve them.

According to various embodiments, the app may show the user that the number of steps taken has been exceeded or fallen short. In the case of underachievement, the app may show the user how far away from his goal he is. According to various embodiments, users may be provided with a visual motivation and regional/targeted marketing (for example marketing information) to accomplish predefined health related goals.

According to various embodiments, visualized motivation may take the form of notification to the user how far the user is short of the predefined goals and how the goals can be achieved. For example, the user may only need to walk to ABC Subway station in order to achieve this goal. The GPS tracker may identify the current location of the user and may calculate the nearest public place of interest/destination in order to achieve the goal. According to various embodiments, the user may be provided with a visualized motivation in the form of regional/targeted marketing. The user may only need to walk to ABC Bistro Café/ABC Shopping Mall in order to achieve the goal. The GPS tracker may identify the current location of the user and may calculate the nearest market participant or merchants in order to achieve this goal. The merchant may also provide information in the form of deals or discounts to the user as a form of incentive to achieve this goal.

According to various embodiments, a method of accomplishing a fitness goal on a fitness-related application may be provided, the method including the following (for example the following steps):

1. Identify location of user;
2. Monitor user activity of user such that when user activity reaches a predetermined level of user activity;
3. Notify user with a visual notification on shortfall/accomplishment in achieving fitness goal; and
4. Wherein a shortfall is identified, to notify the user to walk to the nearest place of interest or participating merchant to achieve/overachieve fitness goal.

The following examples pertain to further embodiments.

Example 1 is a mobile device comprising: a location determination circuit configured to determine a location of the mobile device; a goal determination circuit configured to determine a goal of a user of the mobile device; a target determination circuit configured to determine a target based on the determined location and based on the determined goal; and a notification circuit configured to notify the user about the target.

In example 2, the subject-matter of example 1 can optionally include that the goal comprises at least one item selected from a group of items consisting of: a fitness goal; a goal related to amount of exercise; a goal related to distance walked; a goal related to energy consumption; and a goal related to steps taken.

In example 3, the subject-matter of any one of examples 1 to 2 can optionally include that the target comprises at least one item selected from a list of items consisting of: a building; a park; a shop; a shopping center; an office; a street; a district of a city; a city; a country; and a state.

In example 4, the subject-matter of any one of examples 1 to 3 can optionally include that the notification circuit is configured to notify the user with an indication related to fulfillment of the goal if the user moves to the determined target.

In example 5, the subject-matter of any one of examples 1 to 4 can optionally include that the location determination circuit is configured to determine the location of the mobile device using at least one of GPS, WiFi triangulation, and mobile radio communication cell triangulation.

In example 6, the subject-matter of any one of examples 1 to 5 can optionally include that the target determination circuit is configured to determine the target so that the determined goal is fulfilled if the user moves to the target.

In example 7, the subject-matter of any one of examples 1 to 6 can optionally include that the target determination circuit is configured to determine a plurality of targets so that the determined goal is fulfilled if the user moves to the plurality of targets.

In example 8, the subject-matter of any one of examples 1 to 7 can optionally include that the target determination circuit is configured to determine a plurality of targets and a sequence of the plurality of targets so that the determined goal is fulfilled if the user moves to the plurality of targets in the sequence.

In example 9, the subject-matter of any one of examples 1 to 8 can optionally include that the notification circuit is configured to notify the user visually.

In example 10, the subject-matter of any one of examples 1 to 9 can optionally include that the mobile device comprises at least one device selected from a group of devices consisting of: a mobile radio communication device; a mobile phone; a tablet computer; a handheld device; and a wearable device.

In example 11, the subject-matter of any one of examples 1 to 10 can optionally include that the target determination circuit is further configured to determine the target further based on traffic conditions.

In example 12, the subject-matter of any one of examples 1 to 11 can optionally include that the target determination circuit is further configured to determine the target further based on weather conditions.

In example 13, the subject-matter of any one of examples 1 to 12 can optionally include that the target determination circuit is further configured to determine the target further based on a time left to complete the goal.

Example 14 is a method for controlling a mobile device, the method comprising: determining a location of the mobile device; determining a goal of a user of the mobile device; determining a target based on the determined location and based on the determined goal; and notifying the user about the target.

In example 15, the subject-matter of example 14 can optionally include that the goal comprises at least one item selected from a group of items consisting of: a fitness goal; a goal related to amount of exercise; a goal related to distance walked; a goal related to energy consumption; and a goal related to steps taken.

In example 16, the subject-matter of any one of examples 14 to 15 can optionally include that the target comprises at least one item selected from a list of items consisting of: a building; a park; a shop; a shopping center; an office; a street; a district of a city; a city; a country; and a state.

In example 17, the subject-matter of any one of examples 14 to 16 can optionally include that notifying the user comprises notifying the user with an indication related to fulfillment of the goal if the user moves to the determined target.

In example 18, the subject-matter of any one of examples 14 to 17 can optionally include that determining the location comprises determining the location of the mobile device using at least one of GPS, WiFi triangulation, and mobile radio communication cell triangulation.

In example 19, the subject-matter of any one of examples 14 to 18 can optionally include that determining the target comprises determining the target so that the determined goal is fulfilled if the user moves to the target.

In example 20, the subject-matter of any one of examples 14 to 19 can optionally include determining a plurality of targets so that the determined goal is fulfilled if the user moves to the plurality of targets.

In example 21, the subject-matter of any one of examples 14 to 20 can optionally include determining a plurality of targets and a sequence of the plurality of targets so that the determined goal is fulfilled if the user moves to the plurality of targets in the sequence.

In example 22, the subject-matter of any one of examples 14 to 21 can optionally include that notifying the user comprises notifying the user visually.

In example 23, the subject-matter of any one of examples 14 to 22 can optionally include that the mobile device comprises at least one device selected from a group of devices consisting of: a mobile radio communication device; a mobile phone; a tablet computer; a handheld device; and a wearable device.

In example 24, the subject-matter of any one of examples 14 to 23 can optionally include determining the target further based on traffic conditions.

In example 25, the subject-matter of any one of examples 14 to 24 can optionally include determining the target further based on weather conditions.

In example 26, the subject-matter of any one of examples 14 to 25 can optionally include determining the target further based on a time left to complete the goal.

Example 27 is a computer readable medium including program instructions which when executed by a processor of a mobile device cause the processor to perform: determining a location of the mobile device; determining a goal of a user of the mobile device; determining a target based on the determined location and based on the determined goal; and notifying the user about the target.

In example 28, the subject-matter of examples 27 can optionally include that the goal comprises at least one item selected from a group of items consisting of: a fitness goal; a goal related to amount of exercise; a goal related to distance walked; a goal related to energy consumption; and a goal related to steps taken.

In example 29, the subject-matter of any one of examples 27 to 28 can optionally include that the target comprises at least one item selected from a list of items consisting of: a building; a park; a shop; a shopping center; an office; a street; a district of a city; a city; a country; and a state.

In example 30, the subject-matter of any one of examples 27 to 29 can optionally include that notifying the user comprises notifying the user with an indication related to fulfillment of the goal if the user moves to the determined target.

In example 31, the subject-matter of any one of examples 27 to 30 can optionally include that determining the location comprises determining the location of the mobile device using at least one of GPS, WiFi triangulation, and mobile radio communication cell triangulation.

In example 32, the subject-matter of any one of examples 27 to 31 can optionally include that determining the target comprises determining the target so that the determined goal is fulfilled if the user moves to the target.

In example 33, the subject-matter of any one of examples 27 to 32 can optionally include program instructions which when executed by the processor of the mobile device cause the processor to perform: determining a plurality of targets so that the determined goal is fulfilled if the user moves to the plurality of targets.

In example 34, the subject-matter of any one of examples 27 to 33 can optionally include program instructions which when executed by the processor of the mobile device cause the processor to perform: determining a plurality of targets and a sequence of the plurality of targets so that the determined goal is fulfilled if the user moves to the plurality of targets in the sequence.

In example 35, the subject-matter of any one of examples 27 to 34 can optionally include that notifying the user comprises notifying the user visually.

In example 36, the subject-matter of any one of examples 27 to 35 can optionally include that the mobile device comprises at least one device selected from a group of devices consisting of: a mobile radio communication device; a mobile phone; a tablet computer; a handheld device; and a wearable device.

In example 37, the subject-matter of any one of examples 27 to 36 can optionally include program instructions which when executed by the processor of the mobile device cause the processor to perform: determining the target further based on traffic conditions.

In example 38, the subject-matter of any one of examples 27 to 37 can optionally include program instructions which when executed by the processor of the mobile device cause the processor to perform: determining the target further based on weather conditions.

In example 39, the subject-matter of any one of examples 27 to 38 can optionally include program instructions which when executed by the processor of the mobile device cause the processor to perform: determining the target further based on a time left to complete the goal.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A mobile device comprising:
a location determination circuit configured to determine a location of the mobile device;
a goal determination circuit configured to determine an exercise amount goal of a user of the mobile device;
a target determination circuit configured to determine a plurality of target locations and a sequence of the plurality of target locations based on the determined location and based on the determined exercise amount goal, the sequence of the plurality of target locations defining an order in which the plurality of target locations is to be visited, wherein the target determination circuit is configured to determine the plurality of target locations and the sequence of the plurality of target locations so that the determined exercise amount goal is fulfilled if the user moves to the plurality of target locations according to the order; and
a notification circuit configured to notify the user about the plurality of target locations and the sequence.

2. The mobile device of claim 1,
wherein the exercise amount goal is related to amount of exercise.

3. The mobile device of claim 1,
wherein each of the plurality of target locations comprises at least one item selected from a list of items consisting of: a building; a park; a shop; a shopping center; an office; a street; a district of a city; a city; a country; and a state.

4. The mobile device of claim 1,
wherein the notification circuit is configured to notify the user with an indication related to fulfillment of the exercise amount goal if the user moves to the plurality of target locations according to the order.

5. The mobile device of claim 1,
wherein the location determination circuit is configured to determine the location of the mobile device using at least one of GPS, WiFi triangulation, and mobile radio communication cell triangulation.

6. The mobile device of claim 1,
wherein the notification circuit is configured to notify the user visually.

7. The mobile device of claim 1,
wherein the mobile device comprises at least one device selected from a group of devices consisting of: a mobile radio communication device; a mobile phone; a tablet computer; a handheld device; and a wearable device.

8. The mobile device of claim 1,
wherein the target determination circuit is further configured to determine the plurality of target locations further based on at least one of traffic conditions, weather conditions, or a time left to complete the exercise amount goal.

9. A method for controlling a mobile device, the method comprising:
determining a location of the mobile device;
determining an exercise amount goal of a user of the mobile device;
determining a plurality of target locations and a sequence of the plurality of target locations based on the determined location and based on the determined exercise amount goal, the sequence of the plurality of target locations defining an order in which the plurality of target locations is to be visited, wherein the plurality of target locations and the sequence of the plurality of target locations are is determined so that the determined exercise amount goal is fulfilled if the user moves to the plurality of target locations according to the order; and
notifying the user about the plurality of target locations and the sequence.

10. The method of claim 9,
wherein notifying the user comprises notifying the user with an indication related to fulfillment of the exercise amount goal if the user moves to the plurality of target locations according to the order.

11. The method of claim 9, further comprising at least one of:
determining the plurality of target locations further based on traffic conditions,
determining the plurality of target locations further based on weather conditions, or
determining the plurality of target locations further based on a time left to complete the exercise amount goal.

12. A non-transitory computer readable medium including program instructions which when executed by a processor of a mobile device cause the processor to perform:
determining a location of the mobile device;
determining an exercise amount goal of a user of the mobile device;
determining a plurality of target locations and a sequence of the plurality of target locations based on the determined location and based on the determined exercise amount goal, the sequence of the plurality of target locations defining an order in which the plurality of target locations is to be visited, wherein the plurality of target locations and the sequence of the plurality of target locations are determined so that the determined exercise amount goal is fulfilled if the user moves to the plurality of target locations according to the order; and notifying the user about the plurality of target locations and the sequence.

13. The non-transitory computer readable medium of claim 12, further including program instructions which when executed by the processor of the mobile device cause the processor to perform at least one of:

determining the plurality of target locations further based on traffic conditions, determining the plurality of target locations further based on weather conditions, or determining the plurality of target locations further based on a time left to complete the exercise amount goal.

* * * * *